(12) United States Patent
Timken et al.

(10) Patent No.: US 7,956,230 B2
(45) Date of Patent: Jun. 7, 2011

(54) REDUCTION OF ORGANIC HALIDE CONTAMINATION IN HYDROCARBON PRODUCTS

(75) Inventors: Hye-Kyung C. Timken, Albany, CA (US); Michael S. Driver, San Francisco, CA (US); Thomas V. Harris, Benicia, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 528 days.

(21) Appl. No.: 11/963,134

(22) Filed: Dec. 21, 2007

(65) Prior Publication Data

US 2009/0163750 A1 Jun. 25, 2009

(51) Int. Cl.
*C07C 2/60* (2006.01)
(52) U.S. Cl. ........ 585/712; 585/833; 585/851; 585/852; 585/864; 585/865; 585/866; 585/709; 585/728; 585/729; 585/721; 585/727; 208/262.1
(58) Field of Classification Search .................. 585/728, 585/833, 851, 852, 864, 865, 866, 709, 712, 585/721, 727, 729; 208/162.1, 262.1
See application file for complete search history.

(56) References Cited

U.S. PATENT DOCUMENTS

| | | | |
|---|---|---|---|
| 4,122,245 A | | 10/1978 | Nardi et al. |
| 5,565,617 A | * | 10/1996 | Schmidt et al. ............... 585/802 |
| 5,731,101 A | | 3/1998 | Sherif et al. |
| 5,750,455 A | * | 5/1998 | Chauvin et al. ............... 502/164 |
| 5,817,908 A | * | 10/1998 | Mehlberg ...................... 585/716 |
| 5,994,602 A | * | 11/1999 | Abdul-Sada et al. ......... 585/457 |
| 6,028,024 A | | 2/2000 | Hirschauer et al. |
| 6,235,959 B1 | | 5/2001 | Hirschauer et al. |
| 6,797,853 B2 | | 9/2004 | Houzvicka et al. |
| 7,553,406 B2 | * | 6/2009 | Wasserscheid et al. ....... 208/236 |
| 7,605,297 B2 | * | 10/2009 | Maase et al. .................. 588/318 |
| 2003/0060359 A1 | * | 3/2003 | Olivier-Bourbigou et al. ........... 502/150 |
| 2004/0077914 A1 | * | 4/2004 | Zavilla et al. ................. 585/737 |
| 2004/0133056 A1 | | 7/2004 | Liu et al. |
| 2006/0135839 A1 | * | 6/2006 | Elomari et al. ............... 585/721 |

OTHER PUBLICATIONS

Yves Chauvin, Andre Hirchauer, Helene Olivier; Alkylation of isobutane with 2-butene using 1-butyl-3-methylimidazolium chloride-aluminium chloride molten salts as catalysts; Journal of Molecular Catalysis 92 (1994) 155-165; Elsevier Science B.V., Netherlands.
Peter Wasserscheid, Thomas Welton; Ionic Liquids in Synthesis; 2003; p. 275; Wiley-VCH Verlag GmbH & Co. KGaA.

* cited by examiner

*Primary Examiner* — Glenn A Caldarola
*Assistant Examiner* — Bradley Etherton
(74) *Attorney, Agent, or Firm* — Susan M. Abernathy; Steven H. Roth

(57) ABSTRACT

A method for reducing halide concentration in a hydrocarbon product made by a hydrocarbon conversion process using an ionic liquid catalyst comprising a halogen-containing an acidic ionic liquid comprising: (i) separating at least a portion of the hydrocarbon product from the ionic liquid catalyst used in the hydrocarbon conversion process from the hydrocarbon product; (ii) contacting at least a portion of the separated hydrocarbon product with an ionic liquid catalyst having the same formula as the ionic liquid catalyst used in the hydrocarbon conversion process; (iii) separating at least a portion of the hydrocarbon product from the ionic liquid catalyst of step (ii); and (iv) recovering at least a portion of the separated hydrocarbon product of step (iii) having a halide concentration less than the halide concentration of the hydrocarbon product of step (i) is disclosed.

35 Claims, No Drawings

REDUCTION OF ORGANIC HALIDE CONTAMINATION IN HYDROCARBON PRODUCTS

FIELD OF THE INVENTION

The present invention relates to methods for reducing organic halide concentration in hydrocarbon products made by hydrocarbon conversion processes using ionic liquid catalysts comprising a halogen-containing acidic ionic liquids.

BACKGROUND OF THE INVENTION

Ionic liquids are liquids that are composed entirely of ions. The so-called "low temperature" ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization, acetylation, metatheses, copolymerization, isomerization, olefin hydrogenation, hydroformylation and combinations thereof.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many other. The most catalytically interesting ionic liquids for acid catalysis are those derived from ammonium halides and Lewis acids (such as $AlCl_3$, $TiCl_4$, $SnCl_4$, $FeCl_3$). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245.

Other examples of ionic liquids and their methods of preparation may also be found in U.S. Pat. Nos. 5,731,101; 6,797,853 and in U.S. Patent Application Publications 2004/0077914 and 2004/0133056.

The alkylation of isobutane with butenes and ethylene in ionic liquids has been described in U.S. Pat. Nos. 5,750,455; 6,028,024; and 6,235,959 and open literature (*Journal of Molecular Catalysis*, 92 (1994), 155-165; *"Ionic Liquids in Synthesis"*, P. Wasserscheid and T. Welton (eds.), Wiley-VCH Verlag, 2003, pp 275).

In general, conversion of light paraffins and light olefins to more valuable cuts is very lucrative to the refining industries. This has been accomplished by alkylation of paraffins with olefins, and by polymerization of olefins. One of the most widely used processes in this field is the alkylation of isobutane with $C_3$ to $C_5$ olefins to make gasoline cuts with high octane number using sulfuric and hydrofluoric acids. This process has been used by refining industries since the 1940's. The process was driven by the increasing demand for high quality and clean burning high-octane gasoline.

Alkylate gasoline is a high quality and efficient burning gasoline that constitutes about 14% of the gasoline pool. Alkylate gasoline is typically produced by alkylating refineries isobutane with low-end olefins (mainly butenes). Currently, alkylates are produced by using HF and $H_2SO_4$ as catalysts. Although these catalysts have been successfully used to economically produce the best quality alkylates, the need for safer and more environmentally friendly catalysts systems has become an issue to the industries involved.

SUMMARY OF THE INVENTION

The present invention relates to methods for reducing halide concentration in a hydrocarbon products made by a hydrocarbon conversion processes using ionic liquid catalyst comprising a halogen-containing an acidic ionic liquid comprising: (i) separating at least a portion of the hydrocarbon product from the ionic liquid catalyst used in the hydrocarbon conversion process from the hydrocarbon product; (ii) contacting at least a portion of the separated hydrocarbon product with an ionic liquid catalyst having the same formula as the ionic liquid catalyst used in the hydrocarbon conversion process; (iii) separating at least a portion of the hydrocarbon product from the ionic liquid catalyst of step (ii); and (iv) recovering at least a portion of the separated hydrocarbon product of step (iii) having a halide concentration less than the halide concentration of the hydrocarbon product of step (i).

Other aspects, features and advantages will be apparent from the description of the embodiments thereof and from the claims.

DETAILED DESCRIPTION

Hydrocarbon conversion processes using a halogen-containing acidic ionic liquid catalyst will generally produce a hydrocarbon product having an organic halide impurity content from 50 to 4000 ppm. Examples of such processes include alkylation, polymerization, dimerization, oligomerization, acetylation, metatheses, copolymerization, isomerization, olefin hydrogenation, hydroformylation and other known processes. The presence of organic halides in such products may be undesirable. The present process can be used to reduce the organic halide concentration is such hydrocarbon products.

The present process is being described and exemplified herein in large part by reference to alkylation processes using certain specific ionic liquid catalysts, but such description is not intended to limit the scope of the invention. The organic halide reduction processes described herein may be used for any hydrocarbon product having an organic halide content from 50 to 4000 ppm which are made by hydrocarbon conversion processes using ionic liquid catalysts comprising halogen-containing acidic ionic liquids as will be appreciated by those persons having ordinary skill based on the teachings, descriptions and examples included herein.

In general, a strongly acidic ionic liquid is necessary for paraffin alkylation, e.g. isoparaffin alkylation. In that case, aluminum chloride, which is a strong Lewis acid in a combination with a small concentration of a Bronsted acid, is a preferred catalyst component in the ionic liquid catalyst scheme.

As noted above, the acidic ionic liquid may be any acidic ionic liquid. In one embodiment, the acidic ionic liquid is a chloroaluminate ionic liquid prepared by mixing aluminum trichloride (AlCl$_3$) and a hydrocarbyl substituted pyridinium halide, a hydrocarbyl substituted imidazolium halide, trialkylammonium hydrohalide or tetraalkylammonium halide to make an ionic liquid of the general formulas A, B, C and D, respectively,

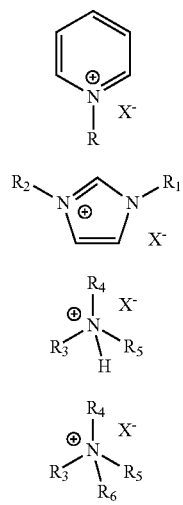

where R═H, methyl, ethyl, propyl, butyl, pentyl or hexyl group and X is a haloaluminate and preferably a chloroaluminate, and R$_1$ and R$_2$═H, methyl, ethyl, propyl, butyl, pentyl or hexyl group and where R$_1$ and R$_2$ may or may not be the same, and R$_3$, R$_4$, and R$_5$ and R$_6$═methyl, ethyl, propyl, butyl, pentyl or hexyl group and where R$_3$, R$_4$, R$_5$ and R$_6$ may or may not be the same.

The acidic ionic liquid is preferably selected from the group consisting of 1-butyl-4-methyl-pyridinium chloroaluminate, 1-butyl-pyridinium chloroaluminate, 1-butyl-3-methyl-imidazolium chloroaluminate and 1-H-pyridinium chloroaluminate. In a process according to the invention an alkyl halide may optionally be used as a promoter.

An alkyl halide is optionally added to the ionic liquid catalyst and acts to promote the alkylation by reacting with aluminum chloride to form the prerequisite cation ions in similar fashion to the Friedel-Crafts reactions. The alkyl halides that may be used include alkyl bromides, alkyl chlorides and alkyl iodides. In aspects of the invention, isopentyl halides, isobutyl halides, butyl halides, propyl halides and ethyl halides may be used. Alkyl chloride versions of these alkyl halides are preferable when chloroaluminate ionic liquids are used as the catalyst systems. Other alkyl chlorides or halides having from 1 to 8 carbon atoms may be also used. The alkyl halides may be used alone or in combination.

A metal halide may be employed to modify the catalyst activity and selectivity. The metal halides most commonly used as inhibitors/modifiers in aluminum chloride-catalyzed olefin-isoparaffin alkylations include NaCl, LiCl, KCl, BeCl$_2$, CaCl$_2$, BaCl$_2$, SrCl$_2$, MgCl$_2$, PbCl$_2$, CuCl, ZrCl$_4$ and AgCl, as described by Roebuck and Evering (Ind. Eng. Chem. Prod. Res. Develop., Vol. 9, 77, 1970). Preferred metal halides are CuCl, AgCl, PbCl$_2$, LiCl, and ZrCl$_4$.

HCl or any Bronsted acid may be employed as co-catalyst to enhance the activity of the catalyst by boasting the overall acidity of the ionic liquid-based catalyst. The use of such co-catalysts and ionic liquid catalysts is disclosed in U.S. Published Patent Application Nos. 2003/0060359 and 2004/0077914. Other co-catalysts that may be used to enhance the activity include IVB metal compounds preferably IVB metal halides such as ZrCl$_4$, ZrBr$_4$, TiCl$_4$, TiCl$_3$, TiBr$_4$, TiBr$_3$, HfCl$_4$, HfBr$_4$ as described by Hirschauer et al. in U.S. Pat. No. 6,028,024.

For example, in the process of producing alkylate hydrocarbon gasoline using haloaluminate ionic liquid catalysts, trace amounts of organic halides are found in the alkylate hydrocarbon. Removal of organic halides from gasoline is desirable to meet product specifications. Analogous results will occur, of course, when ionic liquid catalysts containing halides other than chlorides are used.

In an aspect, the ionic liquid catalyst contains chlorides; the organic halides that contaminate the resulting product are organic chlorides. The chloride content in an alkylate hydrocarbon stream prepared using a chloroaluminate ionic liquid catalyst is generally from 50 ppm to 4000 ppm. Removal of trace organic chlorides from alkylate is also desirable since organic chlorides may generate corrosive or harmful material such as HCl or dioxins during combustion.

In an embodiment, a method for reducing halide concentration in a hydrocarbon product made by a hydrocarbon conversion process using an ionic liquid catalyst comprising a halogen-containing an acidic ionic liquid comprises first separating at least a portion of the hydrocarbon product from the ionic liquid catalyst used in the hydrocarbon conversion process. Then at least a portion of the separated hydrocarbon product is contacted with an ionic liquid catalyst having the same formula as the ionic liquid catalyst used in the hydrocarbon conversion process. This ionic liquid catalyst may be fresh (unused) or regenerated. At least a portion of the hydrocarbon product is separated from the ionic liquid catalyst of the contacting step from which is recovered at least a portion of the separated hydrocarbon product having a halide concentration less than the halide concentration of the hydrocarbon product from the hydroconversion process. In one embodiment, the halide concentration is at least 30% less than the halide concentration of the hydrocarbon product of the hydroconversion process. In an aspect of that embodiment, the halide is a chloride.

In one embodiment, hydrocarbon conversion process conditions include an outlet pressure maintained at about 10 to about 250 psig and the reactor temperature maintained about −10 to about 20° C. The average residence time (combined volume of feeds and catalyst) is about 1-30 minutes.

Contacting can be accomplished by using various devices that provide close contact of the hydrocarbon and ionic liquid catalyst. Such equipment includes, but is not limited to, in-line mixers, stirred tank reactors and nozzle mixers.

Separation of the hydrocarbon product from the ionic liquid catalyst may be accomplished by any method. Some methods and devices that are useful to achieve the separation include settlers and decanters allowing enough residence time for the two phases to separate. The separator may be integral with the contactor as in a counter current extraction device or be a separate unit.

In an embodiment, the ionic liquid catalyst further comprises a co-catalyst selected from the group consisting of Bronsted acids, organic halides and their mixtures thereof. The ionic liquid catalyst used for the contacting step can be a fresh (unused) catalyst or a regenerated catalyst. The ionic liquid catalyst can be a pyridinium chloroaluminate. The co-catalyst used can be butyl chloride. The hydrocarbon conversion process is selected from the group consisting of alkylation, polymerization, dimerization, oligomerization, acetylation, metatheses, copolymerization, isomerization, olefin hydrogenation, hydroformylation and combinations thereof.

Hydrocarbon conversion conditions for these processes are well known to persons of ordinary skill in the art.

In a second embodiment, an alkylation process comprises contacting a first hydrocarbon feed comprising at least one olefin having from 2 to 6 carbon atoms and a second hydrocarbon feed comprising at least one isoparaffin having from 3 to 6 carbon atoms with a halogen containing acidic ionic liquid catalyst under alkylation conditions to produce an alkylate having an organic halide content from 50 to 4000 ppm. At least a portion of the alkylate is separated from the ionic liquid catalyst. Then at least a portion of the separated alkylate is contacted with an ionic liquid catalyst having the same formula as the ionic liquid catalyst used for production of the alkylate. At least a portion of the alkylate is separated from the ionic liquid from which at least a portion of the separated alkylate is recovered. This recovered alkylate has a halide concentration less than the halide concentration of alkylate produced by the alkylation step. In an aspect, the halide concentration in the alkylate after contacting and separation is at least 30% less than the halide concentration of the alkylate as initially produced.

In an embodiment, the alkylation conditions include an outlet pressure maintained at about 30 to about 200 psig and the reactor temperature maintained about 0 to about 20° C. using external cooling. A molar ration of about 6:1 to about 10:1 of isobutane and olefin mixture is fed to the reactor with vigorous stirring. The average residence time (combined volume of feeds and catalyst) is about 1-30 minutes.

Contacting can be accomplished by using various devices that provide close contact of the hydrocarbon and ionic liquid catalyst. Such equipment includes, but is not limited to, in-line mixers, stirred tank reactors and nozzle mixers.

Separation of alkylate from ionic liquid catalyst may be accomplished by any method. Some methods and devices that are useful to achieve the separation include settlers and decanters allowing enough residence time for the two phases to separate. The separator may be integral with the contactor as in a counter current extraction device or be a separate unit.

The following Examples are illustrative of the present invention, but are not intended to limit the invention in any way beyond what is contained in the claims which follow.

EXAMPLE 1

21.9 g of N-butylpyridinium chloroaluminate ($C_5H_5C_4H_9Al_2Cl_7$) ionic liquid catalyst having the following composition

| | |
|---|---|
| Wt % Al | 12.4 |
| Wt % Cl | 56.5 |
| Wt % C | 24.6 |
| Wt % H | 3.2 |
| Wt % N | 3.3 | was added to a closed container under $N_2$ atmosphere. Then 4.6 g of t-butyl chloride was added and the mixture was stirred for 5 minutes to produce a uniform mixture. The mixture was allowed to sit for 20 minutes to overnight under $N_2$ atmosphere to determine whether the mixture would separate into the ionic liquid phase and the hydrocarbon phase. The mixture remained uniform and did not separate demonstrating that ionic liquid could be an effective absorbent for organic chloride species.

EXAMPLE 2

Alkylation of Isobutane with $C_3$-$C_5$ Olefins Using Ionic Liquid Catalyst

Paraffin feed containing predominantly isobutane and an olefin feed containing predominantly $C_3$, $C_4$, and $C_5$ olefins were obtained from a refinery. The feed properties are as follows:

TABLE 1

| Properties of Feeds for Alkylate Gasoline Synthesis | | |
|---|---|---|
| | Paraffin Feed | Olefin Feed |
| | wt % | |
| C1 | 0.04 | 0.30 |
| C2 | 0.05 | 0.05 |
| C3 | 6.8 | 5.80 |
| iC4 | 86.63 | 43.08 |
| nC4 | 5.84 | 12.07 |
| iC5 | 0.44 | 0.80 |
| nC5 | 0.01 | 0.03 |
| C6+ | 0.01 | 0.02 |
| C3= | 0.06 | 4.71 |
| C4= | 0.12 | 32.67 |
| C5= | 0.00 | 0.21 |
| acetylene | 0.00 | 0.01 |
| butadiene | 0.00 | 0.25 |
| Sum | 100.00 | 100.00 |

$C_3$-$C_5$ olefin alkylation with isobutane was performed in a 300 cc continuously stirred tank reactor. An 8:1 molar ratio of isobutane and olefin mixture was fed to the reactor while vigorously stirring at 1900 RPM. The ionic liquid catalyst of Example 1 was fed to the reactor via a second inlet port targeting to occupy 4-10 vol % in the reactor. The average residence time (combined volume of feeds and catalyst) was about 4-20 minutes. The outlet pressure was maintained at 50-150 psig using a backpressure regulator. The reactor temperature was maintained at 0° C. using external cooling. About 100% conversion of olefin was observed, alkylate yield was nearly 200 wt % as predicted from the alkylation chemistry. The resulting alkylate gasoline had a chloride content in the range of 50-2000 ppm.

EXAMPLE 3

Chloride Reduction in a First Batch Test

A 300 mL autoclave was dried and taken into an inert atmosphere glove box. The autoclave was charged with 20 mL of ionic liquid catalyst and 200 mL of an alkylate gasoline sample containing 340 ppm chloride. The autoclave was then sealed, removed from the glove box and stirred at 1500 RPM at room temperature (17° C.). The extraction (contacting) was run between 15 minutes and 60 minutes. The stirring was then stopped and the contents of the autoclave were allowed to sit and gravity separate for 3 minutes. The autoclave was then opened and the alkylate gasoline layer was collected and analyzed by X-ray fluorescence spectroscopy (XRF) and gas chromatography. The XRF showed that the chloride level of the gasoline sample had been reduced as shown in Table 2. The gas chromatograph showed that the alkylate gasoline sample was not degraded during the extraction process.

TABLE 2

Reduction of Chloride in Alkylate Gasoline in Batch Tests #1

| Contacting Time | % Chloride reduction by XRF |
|---|---|
| Starting Alkylate | 0% |
| 15 min | 81% |
| 30 min | 88% |
| 60 min | 87% |

The above data indicate contacting of ionic liquid with chloride containing alkylate gasoline is effective in reducing the chloride content in the gasoline.

EXAMPLE 4

Chloride Reduction in a Second Batch Test

A 300 mL autoclave was dried, taken into an inert-atmosphere glove box and charged with 20 grams of an alkylate gasoline sample containing 467 ppm of chloride. The autoclave was sealed and removed from the glove box. 120 grams of isobutane was then added to the autoclave. The autoclave was then stirred at 1500 RPM and heated to the extraction temperature. After the autoclave had been at the extraction temperature for 15 minutes, 16.25 grams of ionic liquid catalyst was injected into the autoclave under 150 psi $N_2$ pressure (time=0 sec). The extraction experiment was run for 15 minutes. The stirring was then stopped and the contents of the autoclave were allowed to gravity separate for 2 minutes. The autoclave was then depressurized, opened, and the hydrocarbon layer was collected. The hydrocarbon layer was then stored at 10° C. for 12-16 hours to allow the isobutane to evaporate from the sample while retaining the alkylate gasoline component. The alkylate gasoline was analyzed by X-ray fluorescence spectroscopy (XRF) and gas chromatography. The XRF showed that the chloride level of the gasoline sample had been reduced as shown in Table 3. The gas chromatograph showed that the alkylate gasoline sample was not degraded during the extraction process.

TABLE 3

Reduction of Chloride in Alkylate Gasoline in Batch Tests #2

| temperature | % Chloride reduction by XRF |
|---|---|
| 15° C. | 70% |
| 25° C. | 90% |
| 50° C. | 94% |

The above data indicate contacting of ionic liquid with chloride containing alkylate gasoline is effective in reducing the chloride content in the gasoline.

EXAMPLE 5

Continuous Organic Chloride Removal Process

The evaluation of a continuous organic chloride removal process was performed in a 25 cc continuously stirred tank reactor. An approximate 7:1 molar ratio of isobutane and alkylate gasoline mixture containing 305 ppm chloride was fed to the reactor while vigorously stirring at 1900 RPM. An ionic liquid catalyst was fed to the reactor via a second inlet port targeting to occupy 6 vol % of the reactor volume. The average residence time (combined volume of feeds and catalyst) was about 1 to 5 minutes. The outlet pressure was maintained at 50-75 psig using a back pressure regulator. The reactor temperature was maintained at 10° C. using an external cooling loop. The reactor effluent was then separated into 3 phases; an ionic liquid catalyst phase, a liquid hydrocarbon phase, and a gaseous hydrocarbon phase. The liquid hydrocarbons were collected and analyzed by X-ray fluorescence spectroscopy (XRF) and gas chromatography. The XRF showed that the chloride level of the gasoline sample had been reduced as shown in Table 4. The gas chromatograph showed that the alkylate gasoline sample was not degraded during the extraction process.

TABLE 4

Reduction of Chloride in a Continuous Organic Chloride Removal Process

| sample # | % Chloride reduction by XRF |
|---|---|
| 1 | 84% |
| 2 | 88% |
| 3 | 89% |
| 4 | 91% |
| 5 | 92% |
| 6 | 91% |

The above data indicate contacting of ionic liquid with chloride containing alkylate gasoline is effective in reducing the chloride content in the gasoline.

There are numerous variations on the present invention which are possible in light of the teachings and supporting examples described herein. It is therefore understood that within the scope of the following claims, the invention may be practiced otherwise than as specifically described or exemplified herein.

What is claimed is:

1. A method for reducing halide concentration in a hydrocarbon product made by a hydrocarbon conversion process that is an isoparaffin alkylation using an ionic liquid catalyst comprising a halogen-containing acidic ionic liquid, comprising:
   (i) separating an at least a portion of the hydrocarbon product from the ionic liquid catalyst used in the hydrocarbon conversion process from the hydrocarbon product;
   (ii) contacting the at least a portion of the separated hydrocarbon product of step (i) with an ionic liquid catalyst having the same formula as the ionic liquid catalyst used in the hydrocarbon conversion process;
   (iii) separating an at least a portion of the hydrocarbon product from the ionic liquid catalyst of step (ii); and
   (iv) recovering an at least a portion of the separated hydrocarbon product of step (iii) having a halide concentration less than the halide concentration of the at least a portion of the separated hydrocarbon product of step (i); wherein the halide concentration in the recovered hydrocarbon in step (iv) is at least 30% less than the halide concentration of the hydrocarbon product of step (i).

2. The method of claim 1, wherein the ionic liquid catalyst used for the hydrocarbon conversion process further comprises a co-catalyst selected from the group consisting of Bronsted acids, organic halides and their mixtures thereof.

3. The method of claim 2, wherein the co-catalyst is butyl chloride.

4. The method of claim 1, wherein the ionic liquid catalyst in step (ii) is fresh catalyst.

5. The method of claim 1, wherein the ionic liquid catalyst in step (ii) is regenerated catalyst.

6. The method of claim 1, wherein the ionic liquid catalyst is a pyridinium chloroaluminate.

7. The method of claim 1, wherein the halide is a chloride.

8. The method of claim 1, additionally comprising adding isobutane to the at least a portion of the hydrocarbon product of step (i).

9. The method of claim 1, wherein the contacting is done using vigorous mixing or stirring.

10. The method of claim 9, wherein the contacting is done in an in-line mixer, a stirred tank reactor, or a nozzle mixer.

11. The method of claim 1, wherein the halogen-containing acidic ionic liquid comprises $Al_2Cl_7$.

12. The method of claim 1, wherein the recovered hydrocarbon in step (iv) was not degraded by the contacting in step (ii).

13. An alkylation process comprising:
  (i) contacting a first hydrocarbon feed comprising at least one olefin having from 2 to 6 carbon atoms and a second hydrocarbon feed comprising at least one isoparaffin having from 3 to 6 carbon atoms with a halogen containing acidic ionic liquid catalyst comprising $Al_2Cl_7$ under alkylation conditions to produce an alkylate having an organic halide content from 50 to 4000 ppm;
  (ii) separating an at least a first portion of the alkylate from the ionic liquid catalyst;
  (iii) contacting the at least a first portion of the separated alkylate with an ionic liquid catalyst having the same formula as the ionic liquid catalyst used for production of the alkylate in step (i);
  (iv) separating an at least a second portion of the alkylate from the ionic liquid catalyst after step (ii); and
  (v) recovering an at least a portion of the separated at least a second portion of the alkylate of step (iv) having a halide concentration less than the halide concentration of the at least a first portion of the alkylate of step (ii); wherein the halide concentration in the recovered hydrocarbon in step (v) is at least 30% less than the halide concentration of the alkylate of step (i).

14. The process of claim 13, wherein the ionic liquid catalyst of step (iii) further comprises a co-catalyst selected from the group consisting of Bronsted acids, organic halides and their mixtures thereof.

15. The process of claim 14, wherein the co-catalyst is t-butyl chloride.

16. The process of claim 13, wherein the ionic liquid catalyst of step (iii) is fresh catalyst.

17. The process of claim 13, wherein the ionic liquid catalyst of step (iii) is regenerated catalyst.

18. The process of claim 13, wherein the ionic liquid catalyst of step (iii) is a pyridinium chloroaluminate.

19. The process of claim 13, wherein the alkylate product of step (v) is alkylate gasoline.

20. The process of claim 13, wherein the halide is a chloride.

21. The alkylation process of claim 13, additionally comprising adding isobutane to the at least a portion of the separated alkylate of step (ii).

22. The alkylation process of claim 13, wherein the contacting in step (iii) is done using vigorous mixing or stirring.

23. The alkylation process of claim 22, wherein the contacting in step (iii) is done in an in-line mixer, a stirred tank reactor, or a nozzle mixer.

24. The process of claim 13, wherein the recovered hydrocarbon in step (v) was not degraded by the contacting in step (iii).

25. A method for reducing halide concentration in a hydrocarbon product made by a hydroconversion process, comprising contacting an ionic liquid catalyst that comprises $Al_2Cl_7$ with a halide containing hydrocarbon product in the presence of isobutane, wherein the halide level in the halide containing hydrocarbon product is reduced by 70 wt % or greater and the hydrocarbon product is not degraded.

26. The method of claim 25, wherein the halide is chloride.

27. The method of claim 26, wherein the halide is organic chloride.

28. The method of claim 25, wherein the halide containing hydrocarbon product is an alkylate gasoline.

29. The method of claim 25, wherein the ionic liquid catalyst is a pyridinium chloroaluminate.

30. The method of claim 25, wherein the halide containing alkylate hydrocarbon product has a halide content from 50 ppm to 4000 ppm.

31. The method of claim 25, wherein the halide level in the hydrocarbon product is reduced by 90 wt % or greater.

32. The method of claim 25, wherein the hydrocarbon conversion process is selected from the group consisting of alkylation, polymerization, dimerization, oligomerization, acetylation, metatheses, copolymerization, isomerization, olefin hydrogenation, hydroformylation, and combinations thereof.

33. The method of claim 32, wherein the hydrocarbon conversion process is alkylation.

34. The method of claim 25, wherein the contacting is done using vigorous mixing or stirring.

35. The method of claim 34, wherein the contacting is done in an in-line mixer, a stirred tank reactor, or a nozzle mixer.

* * * * *